United States Patent [19]
Bell

[11] Patent Number: 5,653,231
[45] Date of Patent: Aug. 5, 1997

[54] TRACHEOSTOMY LENGTH SINGLE USE SUCTION CATHETER

[75] Inventor: Craig J. Bell, E. Swanzey, N.H.

[73] Assignee: MedCare Medical Group, Inc., E. Swanzey, N.H.

[21] Appl. No.: 563,572

[22] Filed: Nov. 28, 1995

[51] Int. Cl.$^6$ .................................................. A61M 16/00
[52] U.S. Cl. ........................... 128/207.16; 128/207.15
[58] Field of Search ......................... 128/207.16, 207.14, 128/207.15; 604/21, 35, 119

[56] References Cited

U.S. PATENT DOCUMENTS

| | | | |
|---|---|---|---|
| 3,848,604 | 11/1974 | Sackner | 604/119 |
| 3,911,919 | 10/1975 | Raitto | 604/119 |
| 3,937,220 | 2/1976 | Coyne | 604/119 |
| 4,300,550 | 11/1981 | Gandi et al. | 604/35 |
| 4,512,765 | 4/1985 | Muto | 604/119 |
| 4,691,702 | 9/1987 | Chantzis | 128/207.16 |
| 4,762,125 | 8/1988 | Leiman et al. | 604/35 |
| 5,076,787 | 12/1991 | Overmyer | 604/119 |
| 5,167,622 | 12/1992 | Muto | 604/35 |
| 5,325,850 | 7/1994 | Ulrich et al. | 128/207.16 |
| 5,368,017 | 11/1994 | Sorenson et al. | 128/207.16 |

*Primary Examiner*—Aaron J. Lewis
*Attorney, Agent, or Firm*—George W. Dishong

[57] ABSTRACT

A short, tracheostomy length, single use open suction catheter, made of relatively flexible plastic material such as natural or synthetic rubber, polypropylene, polyethylene, polyvinyl chloride, nylon or like material having the flexibility and resilience necessary for use in the suctioning of the airway of tracheostomized patients in order to remove tracheobronchial secretions from such a patient with a tracheostomy tube in place. The tracheostomy length catheter has a fitting for connecting the proximal end (the end nearest the source of vacuum) to a source of vacuum. There is a valve, such as a thumb controlled valve, at the proximal end used for controlling the extent of the vacuum or low pressure at the distal end of the suction catheter (the end nearest the patient). The valve regulates the vacuum by covering or partially covering a vent port with the thumb of the clinician who is doing the suctioning of the patient. The overall length of the tracheostomy length suction catheter, including the standard thumb valve used to control vacuum (about 4.5 cm in length), is about one-half the length of known and commonly used single use suction catheters which are about about 50 cm to about 61 cm or 20 inches to 24 inches. The overall length of the tracheostomy length suction catheter with the standard thumb valve being about 18.50 cm–40.0 cm or about 7.25 inches–15.75 inches. Further the tracheostomy length suction catheter may incorporate one of a variety of tip designs or components at the distal end thereof to improve the effectiveness of the removal of the secretions and to reduce the mucosa damage.

4 Claims, 5 Drawing Sheets

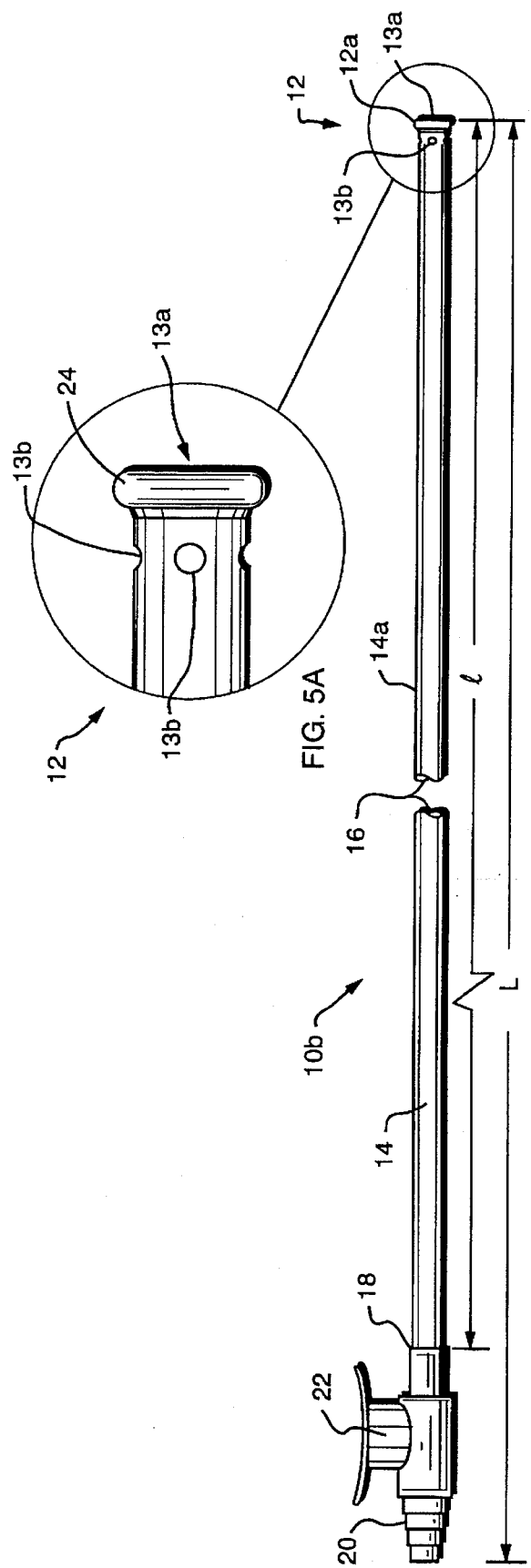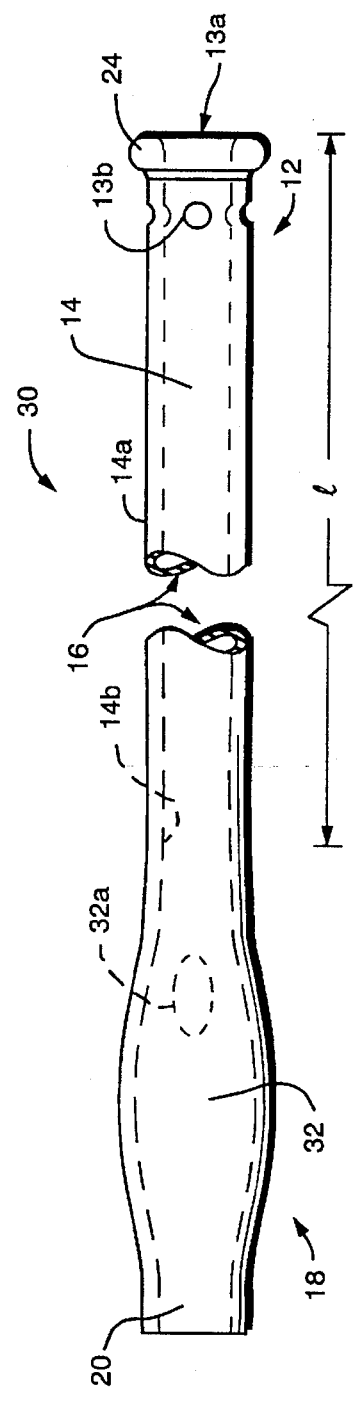

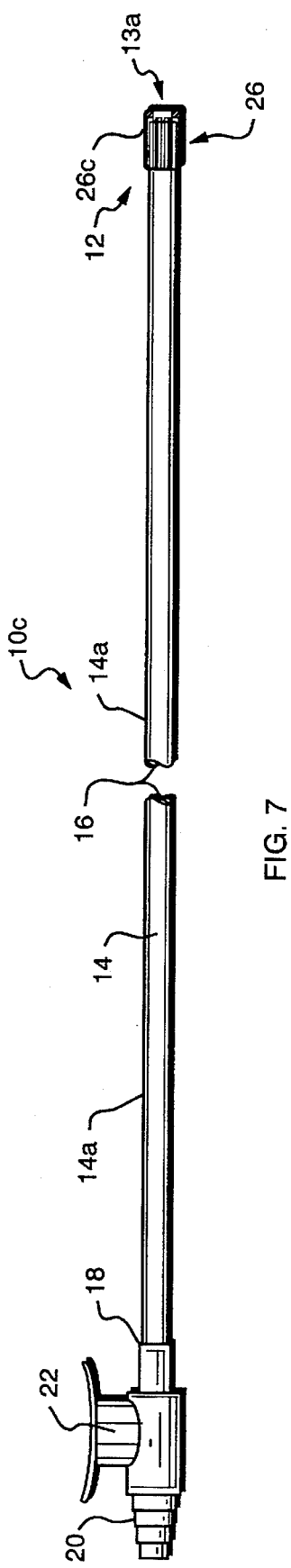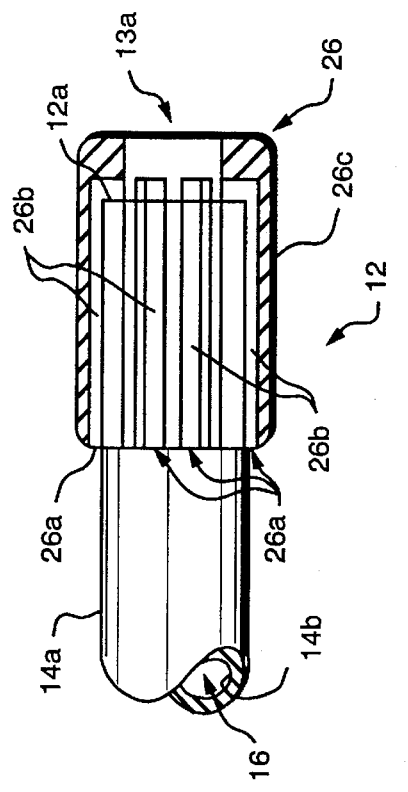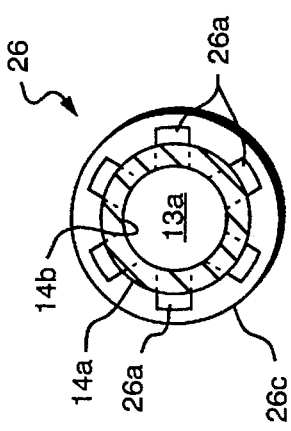
FIG. 7
FIG. 8
FIG. 9

TRACHEOSTOMY LENGTH SINGLE USE SUCTION CATHETER

BACKGROUND OF THE INVENTION

1. Field of the Invention

This invention most generally relates to single use suction catheters. More particularly the invention relates to a construction of a single use open suction catheter for use in the suctioning of the airway of tracheostomized patients in order to remove unwanted tracheobronchial secretions from such a patient with the tracheostomy tube in place. Most particularly, the suction catheter, is about one-half the length of known and commonly used single use suction catheters, having means for connecting the proximal end (the end nearest the source of vacuum) to a source of vacuum, means for controlling the extent of the vacuum or negative/low pressure at the distal end (the end nearest the patient) and further the suction catheter may incorporate one of a variety of tip designs or components at the distal end thereof to improve the patient safety and the effectiveness of the removal of the secretions. The outer surface of the flexible tube and the surface of the lumen running through the tube may be coated with anti-bacterial and/or lubricating materials.

2. Description of the Prior Art

The use of suction catheters to remove tracheobronchial fluid from both the intubated and non-intubated patient is well known in the art. These catheters are made of plastic or rubber and are connected to a vacuum line via a connector or a vacuum control valve. This valve regulates the vacuum by covering a vent port with the thumb of the clinician who is doing the suctioning of the patient. The length of the currently known and widely used catheter is typically 20-24 inches. The length has to be long enough to pass through a swivel access port, nasal length endotracheal tube, and reach the carina (bifurcation of the trachea into the right and left lungs). Thus the currently used catheters are long enough to be used both for the suctioning of the nasopharyngeal airway and the tracheobronchial tree.

No clinician would dispute that suctioning an airway is hazardous. The procedure can cause hypoxemia, cardiac arrhythmias, hypotension, hypertension, damage to the tracheal mucosa, infection, increased intracranial pressure, cardiac arrest, and even sudden cardiac death. A primary goal is to minimize these risks.

The following patents known to inventor hereof, do not in any manner suggest or teach the catheter disclosed and claimed by applicant in the instant application for patent. All of the open, single use suction catheters known to the inventor hereof are of a length sufficient for use with intubated patients being ventilated with an endotracheal tube via the nasal passage, the mouth and throat and also those patients fitted with a tracheostomy tube in which instance the catheter is of considerable excess length.

U.S. Pat. No. 3,848,604, to Sackner, issued Nov. 19, 1974 teaches a suction catheter having a laterally extending flange means and a plurality of apertures through the tube at the distal end to reduce the potential for indrawing of the mucosa into the catheter thereby causing damage to the mucous membrane and mucosa of the tracheobronchial tree.

U.S. Pat. No. 3,991,762, to Radford, issued Nov. 16, 1976 is for a closed suction device having a patient end that fits directly onto the endotracheal connector, a plastic sleeve and a normally closed self biasing suction valve.

U.S. Pat. No. 5,419,314 to Christopher teaches a transtracheal catheter with total length being approximately 20 cm, 20 cm being shorter than conventional transtracheal catheter lengths. It should be noted that Christopher uses the transtracheal catheter to provide ventilation. Particularly, the invention of Christopher is for weaning a patient from a ventilator by augmenting respiration with the flow of supplemental oxygen. At a negative pressure with this device a patient would quickly desaturate. There is no use proposed for suctioning.

U.S. Pat. No. 5,186,168 to Spofford et al, discloses a catheter for providing supplemental oxygen and Spofford et al. teaches that the length may be shorter to prevent certain problems. Again the catheters are not used as single use suction catheters but are used to supply supplemental oxygen to spontaneously breathing patients with chronic lung disorders. Negative pressure delivered with this device would induce hypoxia by removing the patient's oxygen.

U.S. Pat. No. 4,990,143 to Sheridan teaches plastic helix reinforced tubes and that tracheal tubes are made in a variety of sizes, such tubes ranging from about 10 to 40 cm in length.

U.S. Pat. No. 4,796,617 to Matthews et al, discloses a tracheostomy tube assembly and ventilation system and is used to allow the positive pressure oxygen delivery to exit the tip of the device before the carina in order to deliver oxygen to both the right and left lungs. He teaches a tube length that is close to the patient's carina but does not reach it. The tube maximum length is about 100 mm (approximately 4 inches) from the flange. It is suggested that the Matthews device could be used to introduce a suction catheter through for the removal of tracheobronchial secretions. His device could not be used for suctioning.

U.S. Pat. No. 4,691,702 to Chantzis discloses an aspirating device with a desirable catheter length of about 560 mm (22 inches), and further teaches that the length of the catheter will be influenced by compatibility with other respiratory devices being used with the catheter and by accepted medical standards for the procedures being performed. The Chantzis device is a multiple use catheter that is indicated to remain connected to the patient's breathing circuit for an extended time period.

Damage to the tracheal mucosa and to the carina may frequently occur when the single use open suction catheter of known and accepted length (20 inches–24 inches) is used on a tracheostomized patient. The excessive length of the catheter will permit a clinician to insert the catheter tube so far as to "bump" into the carina or pass further into most probably the right bronchial passage. In both instances damage to the mucosa very likely takes place. Such trauma can be very easily eliminated or substantially reduced by using a short open single use suction catheter—a tracheostomy length single use suction catheter according to the catheter disclosed and claimed herein.

There are no patents known to the inventor which cover tracheostomy length single use open suction catheter. It has been apparently unobvious to all in the suction devices market, that a tracheostomy length single use open suction catheter (flexible tube length of between about 5.5 inches and 14.0 inches and an overall length including thumb valve of between about 7.25 inches and 15.75 inches) has considerable advantage over the longer 20 inch–24 inch known single use suction catheter.

It would be advantageous to have a suctioning device and method which would reduce the risk of trauma as a result of using standard suctions catheters with tracheostomized patients. The invention has the particular objectives, features and advantages of: 1) Reduction of patient discomfort; 2) Reduction in tracheal/bronchial mucosa damage because of the shorter length; 3) A substantial increase in suction efficiency—about twenty five percent (25%); 4) Substantially better control of rotation of the distal/patient end (end within patient's airway) from the control valve end such rotation effective to "sweep" the secretions to affect better and more thorough suctioning; 5) Since the catheter is single use and the instant short catheter is about 50% the length of known and used there is a 50% reduction in the amount of waste including storage, shipping cartons, and lower sterilization costs; and 6) Reduction in hospital storage space needed to store disposable single use suction catheters.

The patents noted herein provide considerable information regarding the developments that have taken place in this field of technology. Clearly the instant invention provides many advantages over the prior art inventions noted above. Again it is noted that none of the prior art catheters meets the objects of the short suction catheter in a manner like that of the instant invention. None of them are as effective and as efficient as the instant catheter for use in the suctioning of tracheostomized patients.

SUMMARY OF THE INVENTION

A single use open suction catheter for use in suctioning of excess and undesirable tracheobronchial secretions from the tracheobronchial tree region of a patient having a tracheostomy tube in place. The suction catheter comprises a flexible tube having an outer wall defining an outside diameter which outside diameter is suitable for insertion into the tracheostomy tube and an inner wall surface defining an inner diameter. The inner wall defines thereby a lumen running interiorly therethrough. The flexible tube has two ends, a proximal end and a distal end. There is also means for connecting the lumen to a source of vacuum. The connecting means is securely affixed at the proximal end of the flexible tube. The source of vacuum, when connected via the connecting means creates a negative pressure relative to the pressure within the tracheobronchial tree region of the patient. Further, there is means for regulating the negative pressure when created in the lumen. The means for regulating is located substantially at the proximal end of the tube. Additionally there is means for communicating, at the distal end of the flexible tube, the regulated negative pressure created in the tureen to the tracheobronchial tree region of the patient. Also the length dimension is a so-called tracheostomy length dimension of the flexible tube. Such length is defined between a minimum length of about fourteen centimeters and a maximum length of about thirty five and six tenths centimeters. The tracheostomy length is defined as a distance from the distal end to the proximal end of the flexible tube. Further, the outer surface of the flexible tube and the surface of the lumen running through the tube may be coated with antibacterial and/or lubricating materials.

Objects and advantages of the invention are: 1) Reduction of patient discomfort; 2) Reduction in tracheal/bronchial mucosa damage because of the shorter length; 3) A substantial increase in suction efficiency—about twenty five percent (25% ); 4) Substantially better control of rotation of the distal/patient end (end within patient's airway) from the control valve end such rotation effective to "sweep" the secretions to affect better and more thorough suctioning; 5) Since the catheter is single use and the instant short catheter is about 50% the length of known and used there is a 50% reduction in the amount of waste including storage, shipping cartons, and lower sterilization costs; and 6) Reduction in hospital storage space needed to store disposable single use suction catheters.

A primary object of the invention is to provide an improved single use open suction catheter for use in suctioning of excess and undesirable tracheobronchial secretions from tracheobronchial tree region of a patient having a tracheostomy tube in place. The catheter structure comprises a flexible tube having a lumen running interiorly therethrough. The flexible tube has a distal end and a proximal end, the proximal end having means for connecting to a source of vacuum and means for regulating an amount of vacuum created within the lumen. The distal end is in vacuum flow communication with the lumen and has a distal tip portion. The distal tip portion has at least one axially directed aperture in axial vacuum flow communication with the lumen and the tracheobronchial tree region of the patient. The improvement comprises a tracheostomy length dimension of the flexible tube which is defined between a minimum length and a maximum length. The minimum length is defined substantially by about a distance of about fourteen centimeters (14 cm) from the tracheobronchial tree region to the means for regulating the amount of vacuum and a maximum length less than about thirty five and six tenths centimeters (35.6 cm).

Another primary object of the invention is to provide the improved single use open suction catheter as above wherein the distal tip portion has a plurality of apertures substantially radially directed from the lumen to the tracheobronchial tree region of the patient. Each aperture being proximate to the distal lip portion.

Yet another primary object of the invention is to provide the improved single use open suction catheter as above but wherein the distal tip portion has formed thereon and affixed thereto a tip element. The lip element may be configured as a flange extending radially from the distal end and between the radially directed aperture and each axially directed aperture. Or the distal lip portion may have a chisel shape for the tip end or a blunt tip end depending perhaps upon the application of the catheter. Yet another tip element may be configured to create a plurality of reverse vacuum flow paths by causing vacuum flow and secretions flow into the axially directed aperture in the tip end and providing secretion flow and vacuum air flow over an outer surface of the tip element and into each of a plurality of reverse directing apertures. Each of the plurality of reverse directing apertures is axially configured to cause vacuum air flow toward the distal end and subsequently into the lumen.

A particular object of the present invention is to provide a single use open suction catheter comprising: a flexible tube having an outer wall with a cross section geometry, at any selected location along the flexible tube, selected from the group consisting of circular, oval and elliptical, defining outside dimensions which outside dimensions are suitable for insertion into the tracheostomy tube and an inner wall surface defining a lumed running interiorly therethrough the flexible tube. The flexible tube has a proximal end and a distal end; means for connecting the lumen to a vacuum source, wherein the means for connecting to the vacuum is securely affixed at the proximal end of the flexible tube. Additionally there is means for regulating an amount of negative pressure in the lumen relative to the pressure within the tracheobronchial tree region of the patient when the means for connecting is connected to the vacuum source. The means for regulating is located substantially at the proximal end. This means for regulating may be the known thumb type of valve or a valve which is basically an aperture through the wall of the tube near the proximal end and where flexible tube, in the region of the hole/aperture which forms the valve, may have an oval or elliptical cross section. Such a cross section allows for the technician to more easily rotate the catheter within the tracheostomy tube to better suction the patient. There is further provided means for communicating, at the distal end of the flexible tube, the regulated negative pressure created in the lumen to the tracheobronchial tree region of the patient. And the flexible tube is of a length defined as a tracheostomy length dimension. Such length is between a minimum length and a maximum length. The minimum length is substantially about a distance from the tracheobronchial tree region to the means for regulating the pressure or about fourteen centimeters (14 cm). The maximum length is less than about thirty five and six tenths centimeters (35.6 cm).

These and further objects of the present invention will become apparent to those skilled in the art to which this invention pertains and after a study of the present disclosure of the invention.

BRIEF DESCRIPTION OF THE DRAWINGS

FIG. 5 is a side view of the tracheostomy length single use suction catheter having an axial aperture at a radial flange tip and radially directed apertures proximate the tip portion of the flexible tube of the catheter; FIG. 5A shows an enlarged view of the distal tip portion of the catheter shown in FIG. 5;

FIG. 6 is a side view of the tracheostomy length single use suction catheter having an axial aperture at a radial flange tip and radially directed apertures proximate the tip portion of the flexible tube of the catheter and illustrating a section of the flexible tube having an oval or elliptical geometry for the cross section and also showing an alternate means for regulating the amount of vacuum at the distal end;

FIG. 7 is a side view of the tracheostomy length single use suction catheter having an axial aperture at a tip element which reverse directs vacuum flow;

FIG. 8 is a partial cut-a-way view of the reverse directing tip element; and

FIG. 9 is an end view taken from the proximal end toward the distal end to illustrate the plurality of apertures into which flow vacuum and secretions toward the tip end and subsequently into the lumen of the flexible tube.

DESCRIPTION OF THE PREFERRED EMBODIMENTS

Figure 1:
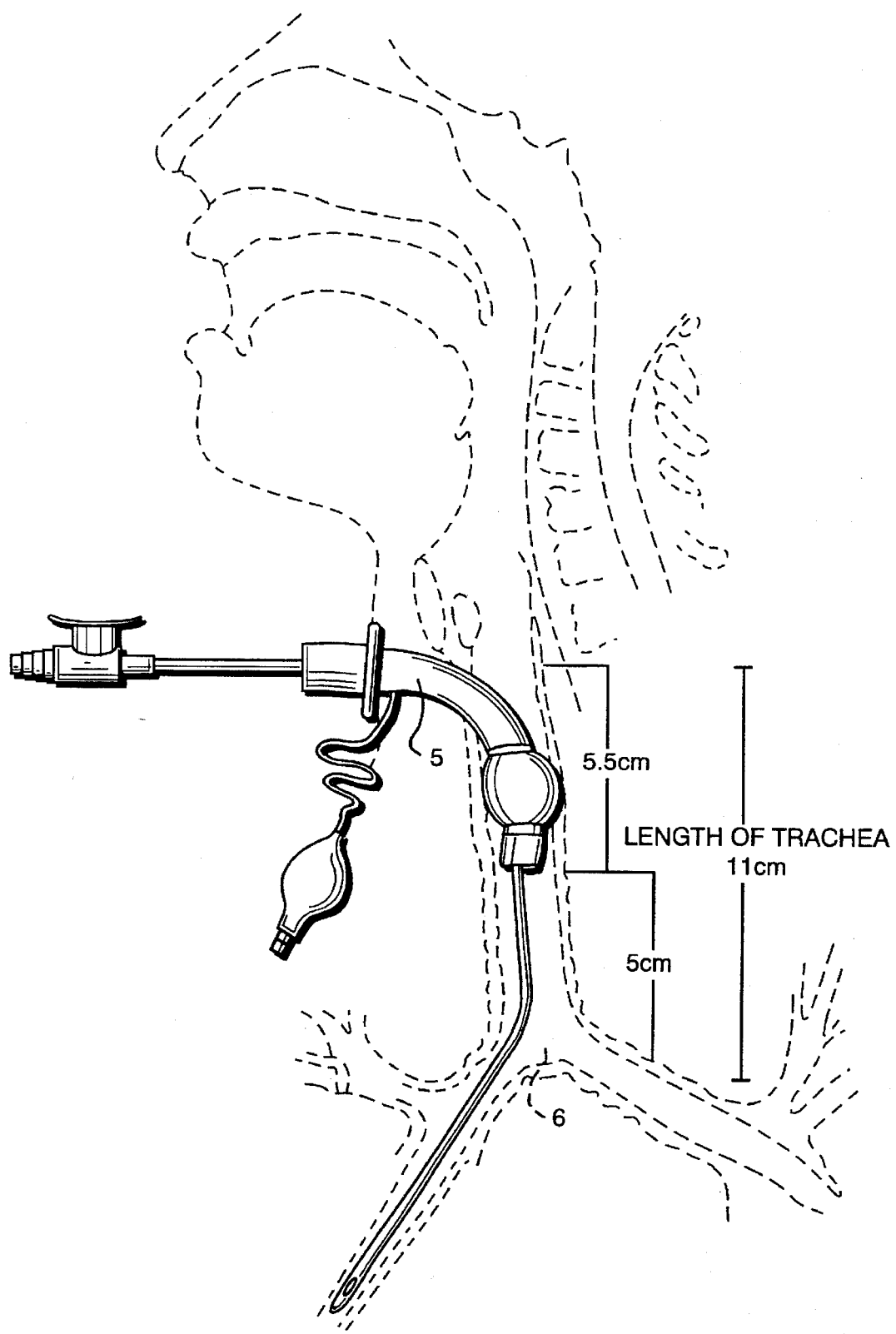
FIG. 1 is a schematic illustration of the use of the known single use suction catheter showing a potential damaging entry of the distal end into the fight bronchus of the patient.

The following is a description of the preferred embodiment of the invention. In order to more clearly define the invention and the use thereof, the following definitions are used in this application. The trachea is the robe within the neck extending from the larynx to the bronchi. A tracheostomy is the construction of an artificial opening through the neck into the trachea, usually made for the relief of difficulty breathing, or it is the name for the opening so constructed. A tracheotomy is the operation of cutting into the trachea. Endotracheal is defined as placed or passing within the trachea, i.e. an endotracheal tube. Therefore a tracheostomy length suction catheter is one designed to be used with a tracheostomy tube inserted through an opening in the neck of a patient, and is therefore considerably shorter than a suction catheter designed to be used with endotracheal tubes inserted through the nose or mouth of a patient. It is clear that there may be variations in the size and the shape of the apparatus, in the materials used in the construction and in the orientation of the components. The cross section of the flexible tube may be other than circular. There may be advantage for example where the tube had a cross section for the entire length or for a portion of the length which is oval or elliptical. However, the main features are consistent and are; an appropriately flexible tube having proper diameter, a distal tip end with either a tip element formed or attached thereto, apertures through which vacuum is communicated to the tracheobronchial region of a patient, means to attach to and control the amount of vacuum communicated to the patient and a length which minimizes the potential for damage to the mucosa of the patient being suctioned. There is also disclosed herein a new tip element which reduces the potential for damage to the membranes within the patient's airway.

Clearly, there are many known materials which are acceptable for use in making such suction catheters. The suction catheters defined herein may be made of relatively flexible plastic material such as natural or synthetic rubber, polypropylene, polyethylene, polyvinyl chloride, nylon or like material having the flexibility and resilience necessary for use in the suctioning of the airway of tracheostomized patients in order to remove tracheobronchial secretions from such a patient with a tracheostomy tube in place. There are many known ways to make connection to a vacuum source and to regulate the amount of vacuum and thus the level of suctioning of the patient. There are also known tip configurations, chisel tip, blunt tip and flange tip all or some of which may help to reduce the potential for damage to the membranes within the patient's airway. It should also be noted that the outer surface of the flexible tube and/or the surface of the lumen may be coated with antibacterial and/or lubricating materials to reduce the potential for infection and to make the catheter more easy to use.

In order to more clearly disclose the invention, known elements such as vacuum power sources, vacuum hoses, and the like will not be shown in the drawings nor discussed to any extent in the description of the invention.

Reference is now made to FIG. 1 which shows how known single use open suction catheters may be misused in the suctioning of tracheostomized patients. Illustrated is the entry of known suction catheter into the right mainstem bronchus of a tracheostomized patient which is wider and shorter and less abrupt in its divergence from the trachea than the left mainstem bronchus which is longer but smaller in caliber than the right. When such an event occurs there is the potential for depletion of the air and oxygen content of the air within the right lung of the patient. While it is more likely that the flexible tube of such a catheter will enter the right bronchus because of the less acute angle formed at the carina, there is a reasonable chance that the flexible tube distal end will enter the longer and more narrow (smaller caliber) left bronchus and likewise deplete the lung but also cause tissue damage due to the inflow of mucous membrane into the apertures on the distal tip of the catheter.

Figure 2:
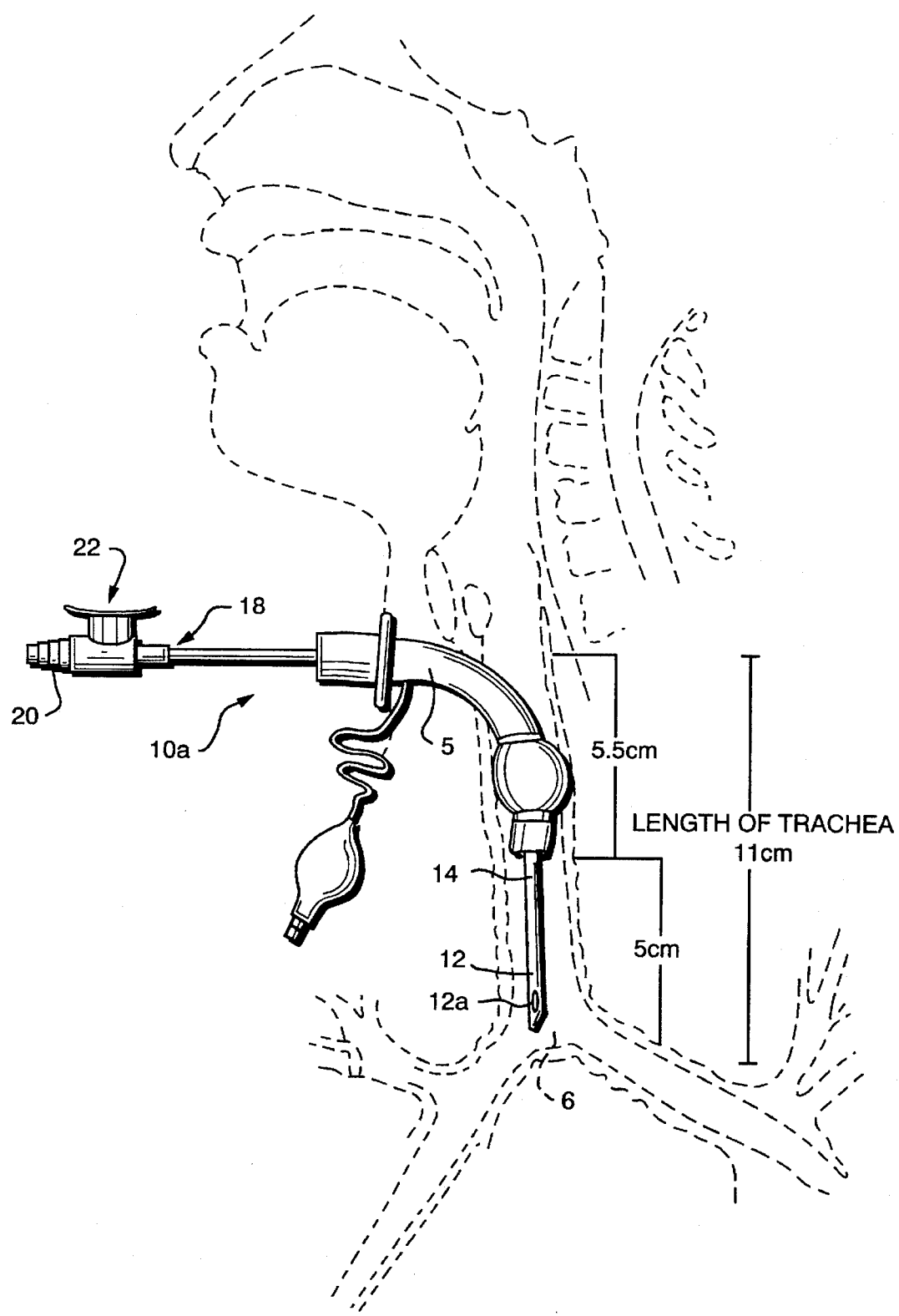
FIG. 2 is a schematic illustration of the use of the tracheostomy length single use open suction catheter according to the present invention showing how the distal end or distal tip of such a catheter comes up short of the carina of the patient.
Figure 3:
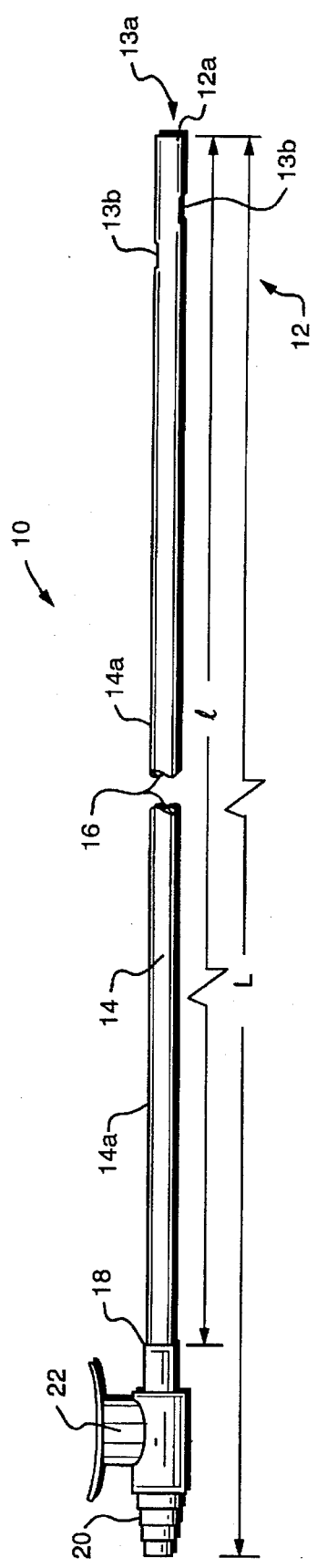
FIG. 3 is a side view of the tracheostomy length single use suction catheter having an axial aperture at a blunt tip and radially directed apertures proximate the tip portion of the flexible tube of the catheter.
Figure 4:
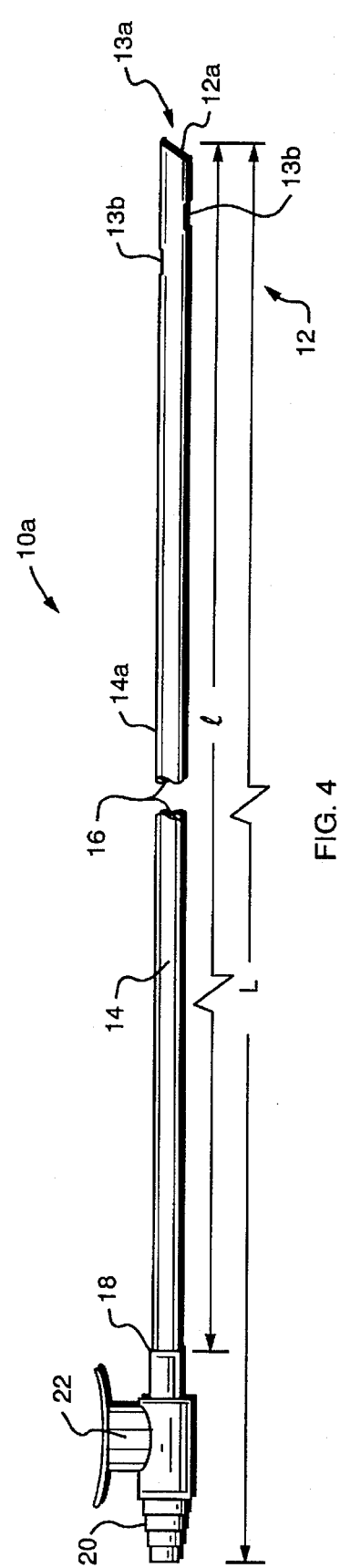
FIG. 4 is a side view of the tracheostomy length single use suction catheter having an axial aperture at a chisel tip and radially directed apertures proximate the tip portion of the flexible tube of the catheter.

FIGS. 2–9 illustrate, by sketch, particular embodiments and features of the present invention. The various embodiments of the tracheostomy length single use open suction catheter are designated by numerals 10, 10a, 10b, 10c and 30. Particularly, FIG. 2 illustrates the particular catheter 10a which has the chisel tip at tip end 12a which is located near the carina and in tracheobronchial tree region 6 of the patient when used to suction unwanted secretions from a patient having a tracheostomy tube 5 in place.

In all the embodiments there is a flexible tube 14, an outer surface 14a of tube 14 and an inner wall 14b forming lumen 16 running through flexible tube 14. Flexible tube 14 has a distal tip portion 12 which in turn has a distal end or distal tip 12a. It is important to note that the length l of flexible tube 14 is defined to reduce the potential for causing entry of tip end 12a into either the fight or the left bronchus and for unnecessary contacting of tip end 12a with the carina. A minimum tracheostomy length l is substantially determined by the distance from tracheobronchial tree region 6 to about the external entry hole of tracheostomy tube 5 when tube 5 is fitted to a smaller patient. This minimum value of tracheostomy length l is defined by about a distance of about fourteen centimeters (14 cm) measured from tip end 12a to proximal end 18 where means for regulating vacuum 22 connects with proximal end 18 of flexible tube 14. A maximum value of tracheostomy length l is defined by about a distance of about thirty five and six tenths centimeters (35.6 cm). An overall length L of catheters 10, 10a, 10b, 10c and 30 which would include means for connecting 20 and means for regulating 22 negative pressure or vacuum of the type illustrated in the drawing figures as catheters 10, 10a, 10b and 10c would be between about eighteen and one half centimeters (18.5 cm) and about forty centimeters (40.0 cm) or about 7.25 inches and about 15.75 inches measured from tip end 12a to the other end of the catheter. If other forms of valves are used overall length L would vary. However, tracheostomy length l is between about 14 cm and about 35.6 cm.

Tip end 12a may have different tip configurations. Catheter 10 has a blunt tip, catheter 10a a chisel tip, catheter 10b and catheter 30 each have a flange tip 24. Catheter 10c has a new tip element—a reverse flow directing tip element 26 which effectively creates a reverse flow of vacuum and unwanted secretions over outer surface 26c of reverse flow directing tip element 26 into each of a plurality of reverse flow directing apertures 26a, through each of a plurality of reverse vacuum flow directing paths 26b and subsequently into lumen 16 of flexible tube 14. Catheters 10, 10a, 10b and 30 have a plurality of radially directed apertures 13b located on distal tip portion 12. All of the catheters have an axially directed aperture 13 at tip end 12b.

At the other end of flexible tube 14 is a proximal end 18. In each of the embodiments there is also a means to connect 20 catheters 10, 10a, 10b, 10c and 30 to a source of vacuum. Such means for connecting 20 may take any known configuration for connecting a flexible vacuum line from the source of vacuum such as a standard vacuum pump to catheters 10, 10a, 10b, 10c and 30. Neither connecting tubing nor the source of vacuum/vacuum pump are shown. Likewise, at proximal end 18 of each of the embodiments of the catheters 10, 10a, 10b, 10c and 30 there is a means for regulating 22 the vacuum amount or the reduced pressure ultimately developed at the tracheobronchial tree region 6 of the patient,. Catheters 10, 10a, 10b and 10c are shown having regulating means 22 being a thumb valve of the type well known to the people in this field. Generally the thumb of the user will be caused to cover or partially cover the vacuum relief opening thereby regulating the mount of vacuum at the tracheobronchial tree region 6 of the patient. Catheter 30 illustrates a regulating valve means 22 which is comprised of vacuum relief aperture 32a located at proximal end 18 and in a region of flexible tube 14 which has a cross section which is oval or elliptical 32. The clinician using catheter 30 would adjust or regulate the vacuum amount by covering or partially covering aperture 32a.

It is thought that the present tracheostomy length single use open suction catheters, for use in the suctioning of tracheostomized patients and many of its attendant advantages is understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

I claim:

1. A single use open suction catheter comprising:

a flexible tube having an outer wall with a cross section geometry, at any selected location along said flexible tube, selected from the group consisting of circular, oval and elliptical, defining outside dimensions which outside dimensions are suitable for insertion into a tracheostomy tube and an inner wall surface defining a lumen running interiorly therethrough said flexible tube, said flexible tube having a proximal end and a distal end;

means for connecting said lumen to a vacuum source, said means for connecting securely affixed at said proximal end of said flexible tube;

means for regulating an amount of negative pressure in said lumen relative to a pressure within a patient's tracheobronchial tree region when said means for connecting is connected to a vacuum source, said means for regulating located substantially at said proximal end;

means for communicating, at said distal end of said flexible tube, said regulated negative pressure created in said lumen to a patient's tracheobronchial tree region; and a tracheostomy length dimension of said flexible tube defined between a minimum length and a maximum length, said minimum length defined substantially by about a distance from a patient's tracheobronchial tree region to said means for regulating said negative pressure, about fourteen centimeters (14 cm) and said maximum length less than about thirty five and six tenths centimeters (35.6 cm);

wherein said means for communicating, at said distal end of said flexible tube, said regulated negative pressure comprises at least one axially directed aperture in axial vacuum flow communication with said lumen and a patient's tracheobronchial tree region;

wherein said single use open suction catheter further comprising a distal tip portion at said distal end, said distal tip portion having a plurality of apertures substantially radially directed from said lumen to a patient's tracheobronchial tree region, each aperture of said plurality of apertures proximate to said distal tip portion; and wherein said distal tip portion has formed thereon and affixed thereto a tip element, said tip element configured as a flange extending radially from said distal end and positioned substantially between said radially directed apertures and each said at least one axially directed aperture.

2. A single use open suction catheter comprising:

a flexible tube having an outer wall with a cross section geometry, at any selected location along said flexible tube, selected from the group consisting of circular, oval and elliptical, defining outside dimensions which outside dimensions are suitable for insertion into a tracheostomy tube and an inner wall surface defining a lumen running interiorly there through said flexible tube, said flexible tube having a proximal end and a distal end;

means for connecting said lumen to a vacuum source, said means for connecting securely affixed at said proximal end of said flexible tube;

means for regulating an amount of negative pressure in said lumen relative to a pressure within a patient's tracheobronchial tree region when said means for connecting is connected to a vacuum source, said means for regulating located substantially at said proximal end;

means for communicating, at said distal end of said flexible tube, said regulated negative pressure created in said lumen to a patient's tracheobronchial tree region;

a tracheostomy length dimension of said flexible tube defined between a minimum length and a maximum length, said minimum length defined substantially by about a distance, from a patient's tracheobronchial tree region to said means for regulating said negative pressure, about fourteen centimeters (14 cm) and said maximum length less than about thirty five and six tenths centimeters (35.6 cm);

wherein said means for communicating, at said distal end of said flexible tube, said regulated negative pressure comprises at least one axially directed aperture in axial vacuum flow communication with said lumen and a patient's tracheobronchial tree region and wherein said single use open suction catheter further comprising a distal tip portion at said distal end, said distal tip portion having a plurality of apertures substantially radially directed from said lumen to a patient's tracheobronchial tree region, each aperture of said plurality of apertures proximate to said distal tip portion; and wherein said distal end has affixed thereto a tip element, said tip element configured to create a plurality of reverse vacuum flow paths by causing vacuum flow and secretions flow into said axially directed aperture in said tip end and providing secretion flow and air flow over an outer surface of said tip element and into each of a plurality of reverse directing apertures, each said plurality of reverse directing apertures being axially configured to cause vacuum air flow toward said distal end and subsequently into said lumen.

3. In an improved single use open suction catheter for use in suctioning of excess and undesirable tracheobronchial secretions from the tracheobronchial tree region of a patient having a tracheostomy tube in place said catheter structure comprising a flexible tube having a lumen running interiorly there through said flexible tube having a distal end and a proximal end, said proximal end having means for connecting to a source of vacuum and means for regulating amount of vacuum created within said lumen, said distal end in vacuum flow communication with said lumen and having a distal tip portion, said distal tip portion having at least one axially directed aperture in axial vacuum flow communication with said lumen and a patient's tracheobronchial tree region, said improvement comprising:

a tracheostomy length dimension of said flexible tube defined between a minimum length and a maximum length, said minimum length defined substantially by about a distance, about fourteen centimeters (14 cm) from a patient's tracheobronchial tree region to said means for regulating said amount of vacuum and a maximum length less than about thirty five and six tenths centimeters (35.6 cm);

wherein said distal tip portion has a plurality of apertures substantially radially directed from said lumen to a patient's tracheobronchial tree region, each aperture of said plurality of apertures proximate to said distal tip portion; and wherein said distal tip portion has formed thereon and affixed thereto a tip element, said tip element configured as a flange extending radially from said distal end and between said radially directed aperture and each said axially directed aperture.

4. In an improved single use open suction catheter for use in suctioning of excess and undesirable tracheobronchial secretions from the tracheobronchial tree region of a patient having a tracheostomy tube in place said catheter structure comprising a flexible tube having a lumen running interiorly there through said flexible tube having a distal end and a proximal end, said proximal end having means for connecting to a source of vacuum and means for regulating amount of vacuum created within said lumen, said distal end in vacuum flow communication with said lumen and having a distal tip portion, said distal tip portion having at least one axially directed aperture in axial vacuum flow communication with said lumen and a patient's tracheobronchial tree region, said improvement comprising:

a tracheostomy length dimension of said flexible tube defined between a minimum length and a maximum length, said minimum length defined substantially by about a distance, about fourteen centimeters (14 cm) from a patient's tracheobronchial tree region to said means for regulating said amount of vacuum and a maximum length less than about thirty five and six tenths centimeters (35.6 cm); and wherein said distal tip portion has formed thereon and affixed thereto a tip element, said tip element configured to create a plurality of reverse vacuum flow paths by causing vacuum flow and secretions flow into said axially directed aperture in said tip end and providing secretion flow and vacuum air flow over an outer surface of said tip element and into each of a plurality of reverse directing apertures, each said plurality of reverse directing apertures being axially configured to cause vacuum air flow toward said distal end and subsequently into said lumen.

* * * * *